(12) United States Patent
Gulabani et al.

(10) Patent No.: US 10,329,672 B2
(45) Date of Patent: Jun. 25, 2019

(54) CORROSION INHIBITING COMPOSITIONS INCLUDING BIS-IMIDAZOLINE COMPOUNDS DERIVED FROM ENRICHED LINEAR TETRAMINES

(71) Applicant: Dow Global Technologies LLC, Midland, MI (US)

(72) Inventors: Ritesh Gulabani, Vadodara (IN); Stephen W. King, League City, TX (US); Prashant Tatake, Hyderabad (IN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/107,741

(22) PCT Filed: Dec. 12, 2014

(86) PCT No.: PCT/US2014/069940
§ 371 (c)(1),
(2) Date: Jun. 23, 2016

(87) PCT Pub. No.: WO2015/100033
PCT Pub. Date: Jul. 2, 2015

(65) Prior Publication Data
US 2016/0333484 A1 Nov. 17, 2016

(30) Foreign Application Priority Data

Dec. 27, 2013 (IN) ............................ 6132/CHE/2013

(51) Int. Cl.
*C23F 11/14* (2006.01)
*C07D 233/10* (2006.01)
(Continued)

(52) U.S. Cl.
CPC .......... *C23F 11/149* (2013.01); *C07D 233/10* (2013.01); *C07D 233/16* (2013.01);
(Continued)

(58) Field of Classification Search
None
See application file for complete search history.

(56) References Cited

U.S. PATENT DOCUMENTS 2,940,927 A * 6/1960 Hughes ................ C07D 233/16
507/243
3,840,382 A * 10/1974 Burke ........................ C08J 3/22
106/431
(Continued)

FOREIGN PATENT DOCUMENTS

CA  2 394 440 A1  7/2002
CA  2 398 423 A1  8/2002
(Continued)

OTHER PUBLICATIONS

Demadis, et al. (2007) "Degradation of Phosphonate-Based Scale Inhibitor Additives in the Presence of Oxidizing Biocides: "Collateral Damages" in Industrial Water Systems", Separation Science and Technology, 42:1639-1649.
(Continued)

*Primary Examiner* — Joseph D Anthony
(74) *Attorney, Agent, or Firm* — Kagan Binder, PLLC

(57) ABSTRACT

The present invention provides corrosion inhibiting compositions that incorporate at least one bis-imidazoline compound. In the practice of the present invention, a tetramine admixture enriched with respect to linear tetramine is used to prepare the bis-imidazoline compound. "Enriched" means at least 70 weight percent and up to 100% of the tetramine species included in the admixture includes a linear tetramine such as L-TETA.

18 Claims, 4 Drawing Sheets

(51) Int. Cl.
  C23F 11/04    (2006.01)
  C09D 5/08    (2006.01)
  C09K 8/54    (2006.01)
  C09K 8/74    (2006.01)
  C23F 11/10    (2006.01)
  C07D 233/16    (2006.01)
  C09D 7/65    (2018.01)

(52) U.S. Cl.
  CPC .............. *C09D 5/086* (2013.01); *C09D 7/65* (2018.01); *C09K 8/54* (2013.01); *C09K 8/74* (2013.01); *C23F 11/04* (2013.01); *C23F 11/10* (2013.01); *C09K 2208/32* (2013.01)

(56) References Cited

U.S. PATENT DOCUMENTS

| | | | |
|---|---|---|---|
| 4,482,724 A * | 11/1984 | Ritschel | B01D 17/047 548/314.4 |
| 4,501,667 A | 2/1985 | Cook | |
| 4,614,600 A | 9/1986 | Schilling et al. | |
| 4,713,184 A | 12/1987 | Zaid | |
| 4,900,458 A * | 2/1990 | Schroeder | C23F 11/14 252/390 |
| 5,611,992 A * | 3/1997 | Naraghi | C09K 8/54 422/15 |
| 5,772,919 A | 6/1998 | Reichgott et al. | |
| 5,922,663 A * | 7/1999 | Gabriel | B01F 17/0021 510/299 |
| 6,040,288 A * | 3/2000 | Popoff | C11D 3/3742 510/323 |
| 6,338,819 B1 * | 1/2002 | Braga | C23F 11/10 252/392 |
| 6,464,901 B1 | 10/2002 | Cheng | |
| 6,475,914 B2 | 11/2002 | Han | |
| 7,682,526 B2 | 3/2010 | Culley et al. | |
| 8,187,997 B2 | 5/2012 | King et al. | |
| 8,188,318 B2 | 5/2012 | Petraitis et al. | |
| 8,293,676 B2 | 10/2012 | King et al. | |
| 2010/0094007 A1 | 4/2010 | King et al. | |
| 2013/0090453 A1 | 4/2013 | Luyken et al. | |
| 2013/0204044 A1 | 8/2013 | Mehta et al. | |

FOREIGN PATENT DOCUMENTS

| | | |
|---|---|---|
| CN | 1584121 A | 2/2005 |
| CN | 101 565 608 A | 10/2009 |
| CN | 101 613 622 A | 12/2009 |
| DE | 3135235 A1 | 3/1983 |
| DE | 40 39 271 A1 | 8/1990 |
| JP | H6268356 A | 9/1994 |
| JP | H09 241636 A | 8/1997 |
| JP | 2000096272 A | 4/2000 |
| MX | PA03011620 A | 6/2005 |
| MX | PA03011659 A | 6/2008 |
| RU | 2357007 C2 | 5/2009 |
| SU | 1526283 A1 | 10/1992 |
| WO | 97/07176 A1 | 2/1997 |
| WO | 00/49204 A1 | 8/2000 |
| WO | 2008/031781 A2 | 2/2008 |
| WO | 2009088702 A1 | 7/2009 |

OTHER PUBLICATIONS

Jawich, et al., "Heptadecyl-tailed Mono-and bis-imidazolines: A study of the newly synthesized compounds on the inhibition of mild steel corrosion in a carbon dioxide-saturated saline medium," Corrosion Science, vol. 65, Dec. 2012, 104-112.

Zhao, et al., "The Synergistic inhibition effect of oleic-based imidazoline and sodium benzoate on mild steel corrosion in a CO2-saturated brine solution," Electrochimic Acta, vol. 69, May 2012, 247-255.

Antonijevic et al., "Copper Corrosion Inhibitors. A Review", International Journal of Electrochemical Science, 3 (Jan. 1, 2008) 1-28.

Farelas et al., "Carbon Dioxide Corrosion Inhibition of Carbon Steels Through Bis-imidazoline and Imidazoline Compounds Studied by EIS", International Journal of Electrochemical Science, 5 (2010) 797-814.

Shin, et al. (1996) "A New Synthetic Route to Poly(benzimidazole) and the Related Model Reactions to Imidazoline and Benzimidazole", Bull. Korean Chem. Soc., 17(1):29-33.

Braddok, et al. (2010) "The reaction of aromatic dialdehydes with enantiopure 1,2-diamines: an expeditious route enantiopure to tricyclic amidines", Tetrahedron: Asymmetry, 21:2911-2919.

\* cited by examiner

CORROSION INHIBITING COMPOSITIONS INCLUDING BIS-IMIDAZOLINE COMPOUNDS DERIVED FROM ENRICHED LINEAR TETRAMINES

CROSS-REFERENCE TO RELATED APPLICATIONS

This application claims priority to International Application No. PCT/US2014/069940, filed Dec. 12, 2014, which in turn claims priority to Indian Patent Application No. 6132/CHE/2013, filed Dec. 27, 2013, wherein the disclosures of these applications are incorporated herein by reference in their respective entireties for all purposes.

FIELD OF THE INVENTION

The present invention relates to corrosion inhibiting compositions that are used to help protect materials such as metals, metal alloys, intermetallic compositions, and the like against corrosion, wherein the compositions comprise one or more bis-imidazolines that are functionalized with hydrophobic moieties on both imidazoline rings of the bis-imidazolines. More particularly, the present invention relates to such corrosion inhibiting compositions in which an amine admixture enriched with respect to linear tetramine is used to prepare the bis-imidazoline(s). The functionality of these as corrosion inhibitors in corrosive media is significantly enhanced in the presence of nonionic surfactants.

BACKGROUND OF THE INVENTION

Water-based compositions are used in many industrial processes to help cool or clean metal components of industrial or residential equipment, shipping containers, plumbing and fixtures, buildings, land-based transportation systems, marine-based systems or habitats, or aeronautical systems or habitats. Water also may be a part of a solvent or other constituent of compositions that are being transported, processed, or otherwise handled by such items. Many types of metal components in such systems may contact water-based compositions including heat exchangers, pipes, tanks, valves, water pumps, pump impellers, propellers, and turbine plates, housings, work surfaces, fasteners, supports, computer components, hardware, etc. Metals include pure metals, alloys, intermetallic compositions, or other metal-containing compositions that are susceptible to corrosion.

Water-based compositions may damage metal components by causing erosion or corrosion of the metal. Corrosion generally is a destructive attack on metal involving oxidation or other chemical attack. Corroded metal components can have reduced functionality, causing inefficiencies or inoperability of the industrial process. Corroded components may need to be discarded, repaired or replaced. In addition, corrosion products accumulate and may decrease the rate of heat transfer between the corroded material and the water or other fluid media. Therefore, corrosion may reduce the efficiency of the system operation where efficient cooling is a factor. Corrosion of metallic components in industrial plants can cause system failures and even plant shutdowns.

The presence of certain species in aqueous media can cause or increase oxidation and thereby accelerate the erosion or corrosion of items at risk. This is relevant to the oil and gas industry. As an increasingly widespread practice, this industry tends to inject carbon dioxide into oil wells to reduce the viscosity of oil. This allows more oil to be recovered, enhancing production. The procedure has significant risks, though. Carbonic acid tends to form when carbon dioxide dissolves in water. Carbonic acid can be even more corrosive than hydrochloric acid at similar pH values. Since water is almost always present in oil well operations, using carbon dioxide to enhance oil recovery increases the risk of carbonic acid formation and hence corrosion to pipelines, e.g., carbon steel pipelines, and other equipment.

Corrosion inhibition is a key requirement in many situations, particularly in industries and application segments in order to maintain the integrity of equipment that handles corrosive chemicals or that is subject to corrosion from aqueous media. The use of corrosion inhibitors is particularly important in the oil and gas industry to help protect pipelines from corrosion. There is a constant and continuing need for improved inhibitor products that can deliver consistent protection against corrosion at lower active dosages as well as under severe application conditions at competitive costs.

SUMMARY OF THE INVENTION

The present invention provides corrosion inhibiting compositions that incorporate at least one bis-imidazoline compound. In the practice of the present invention, an amine admixture enriched with respect to linear tetramine is used to prepare the bis-imidazoline compound. "Enriched" means at least 70 weight percent and up to 100% of the tetramine species included in the admixture includes a linear tetramine such as L-TETA. The tetramine material can be enriched as made. Alternatively, leaner tetramine material can be processed to provide enriched embodiments.

Corrosion inhibiting compositions of the present invention provide many advantages. The compositions provide excellent protection against corrosion or other degradation even in harsh environments. For example, illustrative embodiments provide excellent corrosion protection of ferrous metal-containing materials even when the materials are exposed to aqueous acidic media. Without wishing to be bound by theory, it is believed that the excellent corrosion protection is due, at least in part, to the excellent binding and/or adsorption characteristics of the bis-imidazoline compounds for metal-containing substrates, particularly ferrous metals. As a consequence of such binding or adsorption, the compositions are believed to form a protective film or other barrier to help prevent corrosive contact between the substrate and corrosive media. For this reason, it is also believed that the corrosion inhibiting compositions also would protect against corrosion or other degradation in alkaline media and/or in salt water (e.g., sea water) environments.

The bis-imidazolines of the present invention are very effective corrosion inhibitors, and using the enriched linear tetramine provides a reaction product with higher bis-imidazoline content. An unexpected advantage of using bis-imidazolines derived from enriched linear tetramine in combination with nonionic surfactants is that high levels of corrosion protection can be maintained even when the dosage of the bis-imidazoline is reduced. Comparative samples were not able to maintain such high levels of protection under similar circumstances. Another advantage of deriving the bis-imidazoline(s) from one or more enriched, linear tetramines is that the bis-imidazoline is very easy to make without catalyst or solvent in many modes of practice.

The bis-imidazolines also show better thermal stability than mono-imidazolines. This means the compositions of the present invention offer the potential to provide corrosion protection in harsher environments than mono-imidazolines or product mixtures containing less bis-imidazoline content.

The bis-imidazolines of the present invention demonstrate synergistic corrosion protection in combination with non-ionic surfactants. The combination of nonionic surfactant(s) and the bis-imidazoline compounds of the present invention allows lower dosages of the inhibitor to provide substantially the same level of corrosion protection as higher dosages. This is remarkable because ordinarily, even in the presence of a surfactant, corrosion protection drops off considerably when dosage of a common corrosion inhibitor is reduced.

In one aspect, the present invention relates to a method of making a bis-imidazoline, comprising the steps of:

(a) providing an amine admixture comprising at least one tetramine, wherein at least 70 weight percent of the at least one tetramine comprises a linear tetramine according to the following structure having first and second primary amine moieties and first and second secondary amine moieties:

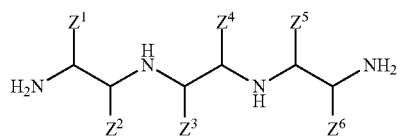

(b) reacting the tetraamine reactant with at least one co-reactive reactant according to the following structure that is monofunctional with respect to carboxylate functionality and that is co-reactive with a primary amine functionality to form an amide linkage:

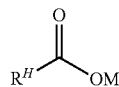

said reaction occurring under conditions effective to form a bis-amide according to the following structure:

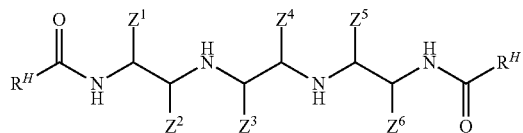

and (c) causing ingredients comprising at least the bis-amide to form a bis-imidazoline according to the following structure:

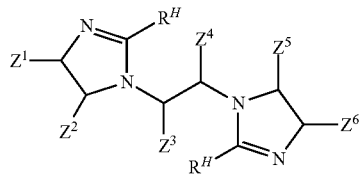

wherein:
each $Z^1$, $Z^2$, $Z^3$, $Z^4$, $Z^5$, and $Z^6$ independently is H; a hydrocarbyl of 1 to 10 carbon atoms; and/or a co-member of a ring structure with another $Z^1$, $Z^2$, $Z^3$, $Z^4$, $Z^5$, or $Z^6$ moiety;

M is a moiety such that the —COOM functionality of the co-reactive reactant is co-reactive with a primary amine functionality of the linear tetramine to form an amide linkage; and each $R^H$ independently is a hydrophobic, aliphatic, monovalent moiety comprising 6 to 50 carbon atoms.

In another aspect, the present invention relates to a method of inhibiting corrosion of a substrate comprising a ferrous metal, the method comprising a step of contacting the ferrous metal with a composition comprising a compound having the following structure:

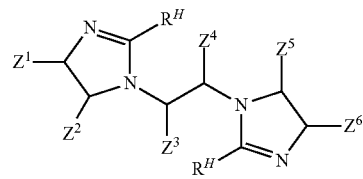

wherein:
each $Z^1$, $Z^2$, $Z^3$, $Z^4$, $Z^5$, and $Z^6$ independently is H; a hydrocarbyl of 1 to 10 carbon atoms; and/or a co-member of a ring structure with another $Z^1$, $Z^2$, $Z^3$, $Z^4$, $Z^5$, or $Z^6$ moiety; and each $R^H$ independently is a hydrophobic, aliphatic, monovalent moiety comprising 6 to 50 carbon atoms.

In another aspect, the present invention relates to a composition having an efficacy for protecting a ferrous metal from corrosion, comprising:

a) an aqueous liquid carrier; and
b) an amount of a bis-imidazoline compound effective to help provide the composition with an ability to inhibit corrosion of the ferrous metal, wherein the bis-imidazoline compound has the following structure:

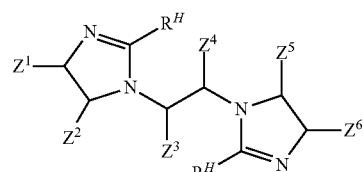

wherein:
each $Z^1$, $Z^2$, $Z^3$, $Z^4$, $Z^5$, and $Z^6$ independently is H; a hydrocarbyl of 1 to 10 carbon atoms; and/or a co-member of a ring structure with another $Z^1$, $Z^2$, $Z^3$, $Z^4$, $Z^5$, or $Z^6$ moiety; and each $R^H$ independently is a hydrophobic, aliphatic, monovalent moiety comprising 6 to 50 carbon atoms.

DETAILED DESCRIPTION OF PRESENTLY PREFERRED EMBODIMENTS

Figure 1:
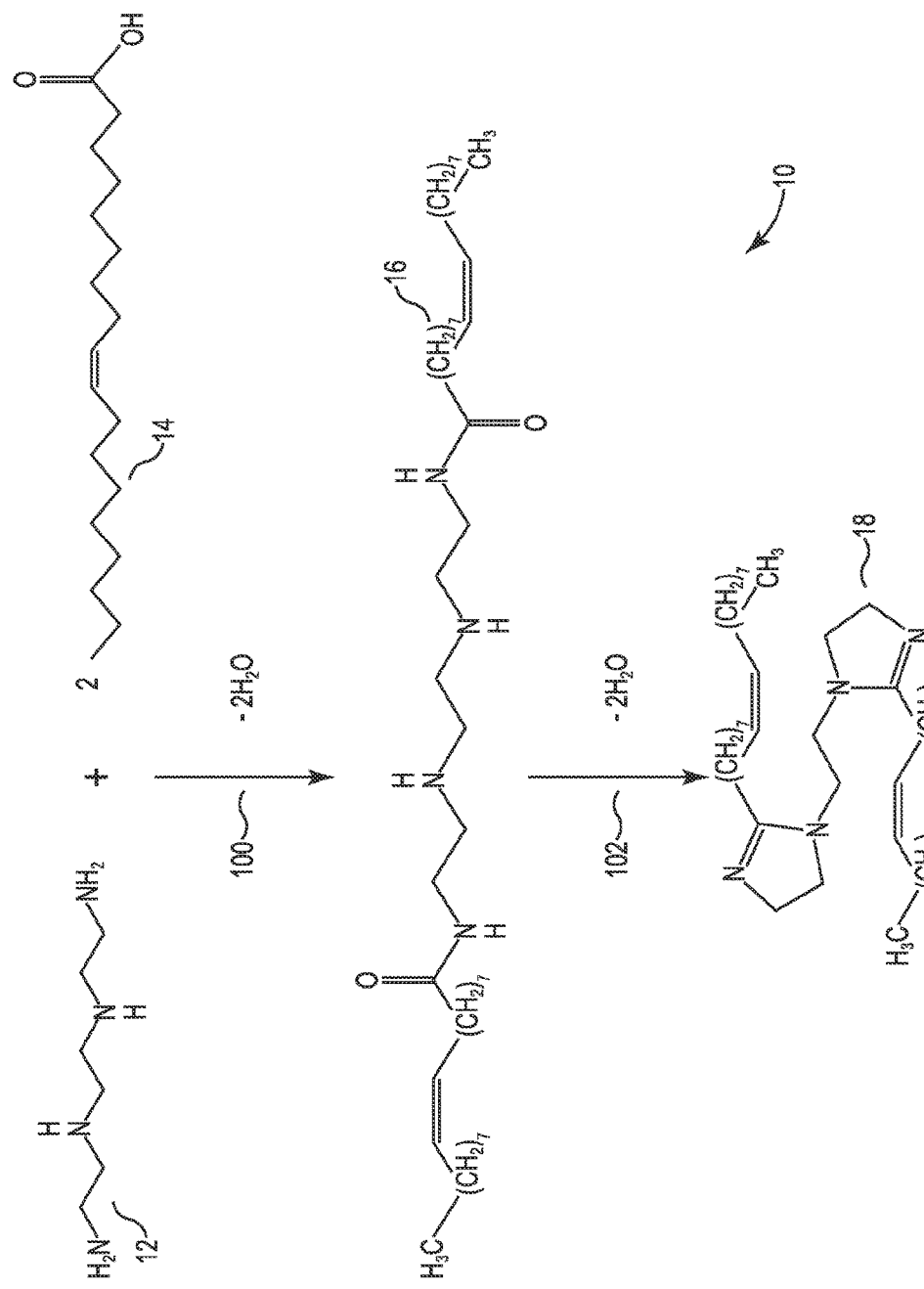
FIG. 1 schematically shows how a bis-imidazoline compound of the present invention is prepared from linear triethylenetetramine (L-TETA) and oleic acid.

The embodiments of the present invention described below are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

In one aspect, the present invention involves the preparation of bis-imidazolines that are useful in treatments that help to protect metal-containing substrates against corrosion. Bis-imidazoline compounds of the present invention include those according to Formula I:

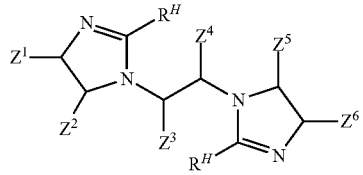

wherein each $Z^1$, $Z^2$, $Z^3$, $Z^4$, $Z^5$, and $Z^6$ independently is a monovalent moiety such as H; a hydrocarbyl of 1 to 10, preferably 1 to 4, and most preferably 1 to 2 carbon atoms; and/or two of the $Z^1$, $Z^2$, $Z^3$, $Z^4$, $Z^5$, and $Z^6$ moieties are linked to each other in a manner effective to form a divalent moiety, such as a hydrocarbylene moiety, that attaches to the corresponding imidazoline ring(s) at two attachment sites. In many embodiments, each $Z^1$, $Z^2$, $Z^3$, $Z^4$, $Z^5$, and $Z^6$ is independently H, methyl, and/or ethyl. A hydrocarbylene moiety is a divalent, saturated hydrocarbon such as —$CH_2$—; —$CH_2CH_2$—; —$CH_2CH_2CH_2$—; —$CH_2CH_2CH_2CH_2$—; —$CH_2CH(CH_3)CH_2CH_2$—; —$CH_2C(CH_3)_2CH_2CH_2$—; —$CH_2CH(CH_3)$ $CH(CH_3)CH_2$—; —$CH_2CH(CH_3)CH_2$—; —$CH(CH_3)CH_2CH_2$—; or the like.

Each $R^H$ independently is a hydrophobic, aliphatic, monovalent moiety comprising 6 to 50, preferably 8 to 30, more preferably 10 to 20 carbon atoms. $R^H$ may be linear, branched or cyclic. $R^H$ may be saturated or unsaturated. Optionally, $R^H$ may include one or more heteroatoms such as O, P, S, N, or the like so long as the heteroatom content is limited so that the $R^H$ moiety is hydrophobic. As used with respect to each $R^H$ moiety, the term hydrophobic means that other than carbon and hydrogen, the moiety includes no more than one other type of atom per every 6 or more, preferably every 8 or more, more preferably every 10 or more carbon atoms. For example, monovalent moieties according to Formula A and Formula B:

Formula A:
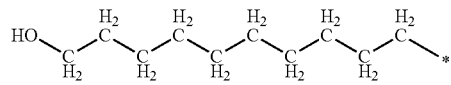

Formula B:
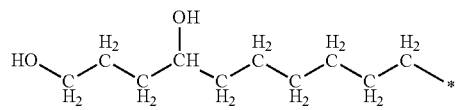

are hydrophobic. Formula A includes 10 carbon atoms per oxygen atom (10:1 ratio). Formula B includes 11 carbon atoms per oxygen atom (11:1 ratio).

In contrast, monovalent moieties according to Formula C and Formula D

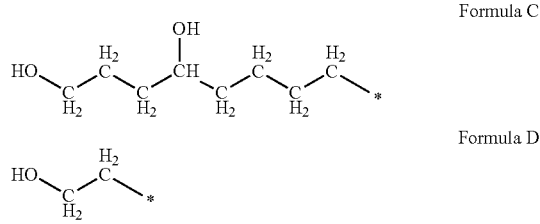

are not hydrophobic. Formula C includes 4 carbon atoms per oxygen atom (4:1 ratio). Formula D includes 2 carbon atoms per one oxygen atom (2:1 ratio).

Unsaturated embodiments of $R^H$ are useful in some embodiments, as corresponding $R^H$ sources (e.g., fatty acids as discussed below) as well as resultant bis-imidazolines may tend to be liquids at room temperature. Exemplary unsaturated embodiments of $R^H$ include one or more of the cis and/or trans versions of one or more of the following:

$CH_3(CH_2)_3CH$=$CH(CH_2)_7$—
$CH_3(CH_2)_5CH$=$CH(CH_2)_7$—
$CH_3(CH_2)_8CH$=$CH(CH_2)_4$—
$CH_3(CH_2)_7CH$=$CH(CH_2)_7$—
$CH_3(CH_2)_7CH$=$CH(CH_2)_7$—
$CH_3(CH_2)_5CH$=$CH(CH_2)_9$—
$CH_3(CH_2)_4CH$=$CHCH_2CH$=$CH(CH_2)_7$—
$CH_3(CH_2)_4CH$=$CHCH_2CH$=$CH(CH_2)_7$—
$CH_3CH_2CH$=$CHCH_2CH$=$CHCH_2CH$=$CH(CH_2)_7$—
$CH_3(CH_2)_4CH$=$CHCH_2CH$=$CHCH_2CH$=$CHCH_2CH$=$CH(CH_2)_3$—
$CH_3CH_2CH$=$CHCH_2CH$=$CHCH_2CH$=$CHCH_2CH$=$CHCHCHCH_2CH$=$CH(CH_2)_3$—$CH_3$    $(CH_2)_7CH$=$CH(CH_2)_{11}$—
$CH_3CH_2CH$=$CHCH_2CH$=$CCHCH_2CH$=$CHCH_2CH$=$CHCH_2CHCH_2CH$=$CH(CH_2)_2$—

Saturated embodiments of $R^H$ also may be useful. Exemplary saturated embodiments of $R^H$ include one or more of $CH_3(CH_2)_6$—
$CH_3(CH_2)_8$—
$CH_3(CH_2)_{10}$—
$CH_3(CH_2)_{12}$—
$CH_3(CH_2)_{14}$—
$CH_3 (CH_2)_{16}$—
$CH_3(CH_2)_{18}$—
$CH_3(CH_2)_{20}$—
$CH_3(CH_2)_{22}$—
$CH_3(CH_2)_{24}$—

Exemplary embodiments of $R^H$ including one or more heteroatoms may include pendant hydroxyl functionality. An example of this kind of $R^H$ moiety is a monounsaturated hydrocarbon chain of 17 carbon atoms (with the first carbon of the chain being attached to the nitrogen of the imidazoline ring in Formula I above or IA below) that includes an OH pendant from the 12th carbon atom of the chain and that includes a double bond between the $8^{th}$ and $9^{th}$ carbons.

Each of the $R^H$ embodiments described above may be sourced from the corresponding fatty acid(s) according to the formula $R^H$—COOM, defined below. Schematically, the $R^H$ moiety can be viewed as the "tail" of the fatty acid. The fatty acids may be used to prepare the bis-imidazoline(s) according to the synthesis schemes described below. In such schemes, the carbon of the COOH group becomes part of an imidazoline ring, and the tail portion becomes an $R^H$ substituent of the ring according to Formula I.

An exemplary compound according to Formula I has the structure shown in Formula IA:

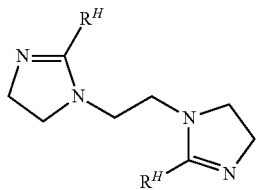

In a preferred embodiment of a compound according to Formula IA, $R^H$ has the cis and/or trans, preferably cis, structure as follows:

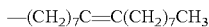

—(CH$_2$)$_7$C═C(CH$_2$)$_7$CH$_3$

The present invention provides methods for preparing bis-imidazolines according to Formula I. In a first step, an enriched tetramine admixture is provided to serve as a reactant for the synthesis of the bis-imidazolines. As used herein, a tetramine is any compound including four amine groups. The tetramine admixture may comprise one or more different tetramines subject to the proviso that the admixture is enriched with respect to one or more linear tetramines according to Formula II, below. In the enriched tetramine admixtures useful in the practice of the present invention, the linear tetramines according to Formula II include primary and secondary amine groups in a manner effective to favor imidazoline ring formation in the reaction scheme described below. However, the enriched tetramine admixtures useful in the practice of the present invention optionally may include one or more other amines, including other tetramines, in which the amine groups may be primary, secondary, and/or tertiary (e.g., aminoethylpiperazine also known as AEP includes tertiary amine content).

One or more of the provided tetramine(s) may be liquid at room temperature. For example, L-TETA (linear, N,N'-bis(2-aminoethyl)-1,2-ethanediamine, also known as linear triethylenetetramine) is a liquid at room temperature. In addition to serving as a tetramine reactant, such a liquid tetramine also may function as a solvent for the reaction, reducing or even eliminating the need for other solvents.

In the practice of the present invention, at least 70% by weight, preferably at least 85% by weight, more preferably at least 95% by weight, and even more preferably at least 99% by weight of the tetramine(s) provided in the first step includes one or more linear, aliphatic tetramines according to Formula II:

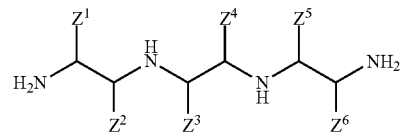

wherein each $Z^1$, $Z^2$, $Z^3$, $Z^4$, $Z^5$, and $Z^6$ independently is as defined above. In an exemplary embodiment, the linear, aliphatic tetramine according to Formula II is linear triethylenetetramine (L-TETA) according to Formula IIA:

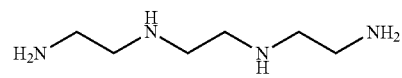

Note that a tetramine according to Formula II has first and second primary amine moieties and first and second secondary amine moieties. Additionally, each primary amine is spaced apart from a corresponding secondary amine by a carbon backbone including 2 carbon atoms. This structure facilitates ring formation as described below.

Tetramine reactants including at least 70% by weight, preferably at least 85% by weight, more preferably at least 95% by weight, and even more preferably at least 99% by weight of the linear, aliphatic tetramine(s) according to Formula II are referred to herein as being enriched. The enriched tetramine(s) may be obtained from one or more source(s). As one option, an enriched tetramine product may be obtained from a commercial source and then purified or otherwise processed to provide an admixture that is enriched with respect to linear tetramine(s). For example, one source is commercially available from The Dow Chemical Co. under the trade designation Amine Multi-Use Emulsifier. This product generally contains 65 weight percent or less of linear tetramines but can be purified or otherwise processed to become enriched. As used herein, a tetramine admixture that has less than an enriched content with respect to linear tetramine according to Formula II will be referred to as being "lean." Techniques for refining lean tetramine sources to produce enriched tetramine material have been described in U.S. Pat. Pub. No. 2013/0204044.

Enriched tetramines also may be manufactured using a variety of different techniques. As one manufacturing option, ethylene dichloride (EDC) may be used to form a product admixture that often is a mixture of amines in which linear tetramines according to Formula II constitute no more than about 65 weight percent of the tetramine content. Accordingly, the lean product mixture obtained from EDC-based processes typically is further refined in order to obtain enriched tetramine material useful in the practice of the present invention. EDC techniques have been described in U.S. Pat. Pub. No. 2013/0204044.

Another useful option for providing enriched tetramine material involves using transamination techniques to form a product admixture that often is a mixture of amines in which linear tetramines according to Formula II constitute more than about 65 weight percent of the tetramine content. An advantage of using transamination techniques is that transamination may directly provide an enriched tetramine product useful in the practice of the present invention. In some modes of practice, transamination provides an enriched tetramine material, but techniques such as those described in U.S. Pat. Pub. No. 2013/0204044 can be practiced to enrich the material even further with respect to linear tetramine content. Transamination techniques useful to form enriched, linear tetramine have been described in U.S. Pat. Pub. No. 2010-0094007-A1, and U.S. Pat. Nos. 8,188,318; 8,293,676 and 8,187,997.

According to another option to provide enriched tetramine composition, U.S. Pat. Pub. No. 2013/0090453 describes a process in which L-TETA is prepared by hydrogenating ethylenediaminediacetonitrile (EDDN) in tetrahydrofuran (THF) in a reactor pressurized with hydrogen. Raney cobalt was used as a catalyst. The product was a mixture of amines including 76.7% TETA.

Subject to the proviso that the tetramine(s) include an enriched amount of one or more linear, aliphatic tetramines according to Formula II, the tetramine(s) provided in the first step optionally may include one or more other linear, branched, or cyclic tetramines. Examples of such other tetramines include one or more of, N,N'-bis-(2-aminoethyl) piperazine (DAEP); N[(2-aminoethyl)$_2$-aminoethyl]piperazine (PEEDA); tris-(2-aminoethyl)amine (TAEA); combinations of these; and the like.

In addition to the tetramines, one or more other amine functional compounds with a greater or lesser number of amine groups than the tetramines can be provided in the first step as well. If present, the weight ratio of tetramine(s) to such other amines may be in the range from 100:0.0001 to 100:50, preferably 100:0.0001 to 100:1. In some modes of practice, these other amines may be monomers, oligomers, and/or polymers. A monomer is a compound including at least one functionality that allows the compound to bond with two or more co-reactive species, that may be the same or different, to form oligomers and polymers. As used herein, an oligomer refers to a compound incorporating two or more monomers (which may be the same or different) and including up to 30 carbon atoms, often 4 to 30 carbon atoms. A polymer refers to a compound incorporating two or more monomers (which may be the same or different) and/or oligomers (which may be the same or different) and including more than 30 carbon atoms. Exemplary amine functional polymers may have a number average weight in the range from 500 to 500,000, sometimes 2000 to 250,000, or sometimes 2000 to 100,000. Gel permeation chromatography (GPC) techniques are useful for determining number average molecular weight in the practice of the present invention.

In a second step, the enriched tetramine admixture is reacted with at least one co-reactive reactant according to Formula III

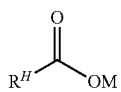

wherein $R^H$ is as defined above and M is any moiety such that the —COOM functionality is co-reactive with a primary amine functionality of the enriched tetramine reactant(s) to form an amide linkage. In many embodiments, M is H, methyl, ethyl, combinations of these or the like. Preferably, M is H. Compounds according to Formula III in which M is H are fatty acids. Accordingly, many useful modes of practice involve reacting one or more linear tetramines according to Formula II with one or more fatty acids according to the formula IIIA

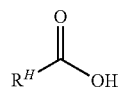

wherein $R^H$ is as defined above.

The reaction between a linear tetramine according to Formula II and a co-reactive reactant according to Formula III forms a bis-amide according to Formula IV

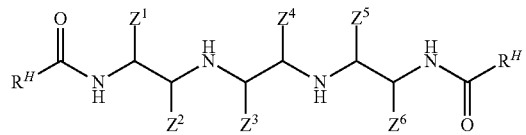

wherein each $R^H$ and each $Z^1$, $Z^2$, $Z^3$, $Z^4$, $Z^5$, and $Z^6$ is independently as defined above. The reaction can occur in a variety of ways. According to one technique, one or more linear tetramines are reacted with a stoichiometric amount of one or more fatty acids (or derivatives of a fatty acid that are co-reactive with the linear tetramine material). The stoichiometric reaction involves two moles of fatty acid (or derivative thereof) reacting with each mole of the tetramine. Although a stoichiometric excess of fatty acid (or derivative thereof) can be used, this is not required or even desirable, as the reaction proceeds to completion without the excess. It is useful to gradually add the tetramine material to the fatty acid (or derivative thereof) rather than to combine the reactants together all at once. This avoids formation of by-products such as amine salt while favoring formation of the bis-amide.

The reaction can occur at a variety of pressures and temperatures for a suitable duration. Suitable temperatures may be in the range from room temperature to about 160° C. One suitable temperature is 150° C. The reaction may occur at ambient pressure, under vacuum, or at elevated pressure. Ambient pressure with good agitation is suitable in many modes of practice. If desired, the reaction may optionally occur in a protected atmosphere, e.g., nitrogen, although this is not required. After all the fatty acid (or derivative) is added to the reaction mixture, the mixture may be held, desirably while being agitated, at one or more reaction temperatures for a sufficient duration to allow the reaction to proceed to a desired degree. In representative modes of practice, this may be from 2 minutes to 48 hours. Maintaining the reaction mixture under the reaction conditions for 4 hours was suitable in one embodiment, for example.

In a third step, the bis-amide according to Formula IV is caused to form a bis-imidazoline according to Formula V

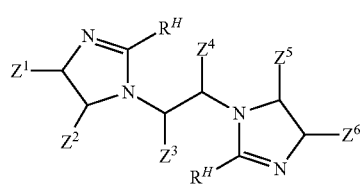

wherein each $R^H$ and each $Z^1$, $Z^2$, $Z^3$, $Z^4$, $Z^5$, and $Z^6$ independently is as defined above. Schematically, the imidazoline rings form when the carbon of each —C(O)— moiety in the compound of Formula IV covalently bonds to the corresponding nitrogen at the corresponding "5" position as schematically shown by the dotted lines in the following Formula IVA:

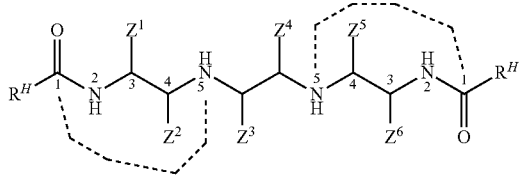

The formation of the bis-imidazoline rings can be accomplished with or without first isolating the bis-amide intermediate. It is convenient in many modes of practice to proceed with ring formation without first isolating the bis-amide. This allows the ring formation to proceed in the same reaction vessel as was used for the formation of the bis-amide.

Ring formation to form the bis-imidazoline can occur under similar conditions regardless of whether the bis-amide is isolated first or not. According to an advantageous technique, ring formation is driven by increasing the temperature of the bis-amide under reduced pressure while removing water by-product to help drive the reaction. Using a combination of elevated temperature and reduced pressure, ring formation occurs even in the absence of catalyst. Suitable temperatures are in the range from 180° C. to 250° C. In one mode of practice, 220° C. was suitable. To help remove water, and thereby to help drive the reaction, the pressure is reduced to any pressure below ambient pressure. In some modes of practice, using a vacuum under 500 mbar (millibar), preferably under 100 mbar, more preferably under 10 mbar, and even more preferably under 1 mbar. The reaction mixture desirably is agitated during at least a portion of the time that the ring formation reaction proceeds.

The ring formation reaction occurs for a sufficient duration to allow the reaction to proceed to a desired degree. In representative modes of practice, this may be from 2 minutes to 48 hours. Maintaining the reaction mixture under the reaction conditions for 5 hours was suitable in one embodiment, for example.

The progress of the ring formation reaction can be monitored using any suitable technique. For example, IR spectroscopy, NMR, and/or liquid chromatography-mass spectrometry (referred to as LCMS or HPLC-MS) can be used to monitor until the amide functionality is reduced to the desired degree. In one mode of practice, the reaction proceeded until no residual amide functionality was detected by LCMS and NMR, indicating substantially complete conversion of the bis-amide to the bis-imidazoline.

Advantageously, no catalyst or solvent is needed to form the bis-amide or bis-imidazoline. Catalysts or solvents could be used if desired, however.

An exemplary reaction scheme 10 to form a bis-imidazoline from L-TETA 12 and oleic acid 14 is shown in FIG. 1. In a first step 100, one mole of L-TETA 12 is reacted with 2 mol of oleic acid 14. The carboxylic acid functionality on the oleic acid 14 reacts with the primary amine functionality on the L-TETA 12 to form a bis-amide intermediate product 16. According to the stoichiometry, two moles of water are produced as a by-product of the amide formation. Next, in reaction step 102, the bis amide product 16 is treated under conditions so that the bis-imidazoline 18 of the present invention is formed. According to the stoichiometry, two moles of water are produced as a by-product of the imidazoline formation.

Additional aspects of the present invention involve corrosion inhibiting compositions incorporating one or more bis-imidazolines according to Formula V. In many embodiments, one or more bis-imidazoline compounds of the present invention are incorporated into an aqueous composition used to help prevent corrosion of a metal material. The aqueous composition can be one that is pre-formed with a desired amount of bis-imidazoline corrosion inhibitor, optionally with one or more other components. The pre-mixed composition can then be used to treat a substrate having one or more metal-containing constituents intended to be protected from corrosion. As another option, an aqueous composition can be formed as a concentrate and then diluted to prepare a formulation more suitable for substrate treatment. In other aspects, an aqueous composition may be generated in situ by adding at least one bis-imidazoline compound on its own or as part of a pre-existing admixture to water already present in a system.

Nonaqueous corrosion inhibiting compositions also are within the scope of the invention. In these, one or more bis-imidazoline compounds of the present invention are incorporated into media in which substantially all of the fluid carrier is an organic solvent such as glycol ethers, heavy oils, hydrocarbons, xylenes, combinations of these, and the like. Other corrosion inhibiting compositions may include solvents that comprise a combination of water and one or more organic liquids in any other suitable proportion. For example, some embodiments may include from about 0.001 to 100 parts by weight of one or more organic liquids per 1 to 100,000 parts by weight of water.

The concentration of the one or more bis-imidazoline compounds added to the composition can vary over a wide range. The concentration may depend on a variety of factors such as the specific compound or combination of compounds used, the presence of other reagents in the composition, the operational parameters of the system using the composition, the type and amount of metal components in the system that are in contact with the composition; or the like. In many useful embodiments such as where an aqueous fluid is flowing through a pipe, the amount of bis-imidazoline compound(s) can be added to the flowing liquid to form a corrosion inhibiting composition in the range of about 0.1 ppm to about 50,000 ppm (i.e., 0.00001 to 5% (wt %)), more preferably in the range of about 1 ppm to about 500 ppm, or from about 1 ppm to about 200 ppm, or about 1 ppm to about 100 ppm. As used herein "ppm" means parts per million on a weight basis relative to the total weight of the composition unless otherwise expressly noted.

In addition to the bis-imidazoline compound(s), a corrosion inhibiting composition can include one or more other ingredients such as those selected from biocides, polymeric dispersants, scale inhibitors, pH adjusters including buffering agents, surfactants, other corrosion inhibiting agents, fungicides, moldicides, antioxidants, UV inhibitors, coloring agents, taggants, gelling agents, etchants, antiskid agents, anti-foam agents, combinations of these, and/or the like.

The corrosion inhibiting compositions preferably include a surfactant. A surfactant can be useful for many reasons, including helping to remove or break up oil deposits on components of cooling water treatment systems. Surfactants can also help to maintain corrosion inhibiting performance even when the concentration of the one or more bis-imidazolines is reduced to atypically low levels. For example, it has been found that using one or more surfactants in combination with a bis-imidazoline according to Formula I allowed a corrosion inhibiting composition to retain over 90 percent inhibition efficiency at a bis-imidazoline concentration of only 3 ppm as compared to a similar composition in which the bis-imidazoline concentration is 10 ppm. This was surprising, as comparison formulations dropped to efficiencies of about 50%, and even 20% or less under similar conditions. In other words, when at least one bis-imidazoline of the present invention used in combination with one or more suitable surfactants, the corrosion inhibiting compositions retain a surprisingly high level of efficiency at lower dosages.

Useful surfactant classes include nonionic surfactants and/or anionic surfactants. Nonionic surfactants are preferred. One preferred nonionic surfactant comprises (a) one or more hydrophilic polyalkylene oxide chains containing on average 2 to 100, preferably 4 to 20 alkylene oxide repeating units, and (b) one or more aromatic hydrophobic moieties. An exemplary nonionic surfactant of this type has a structure according to Formula VI

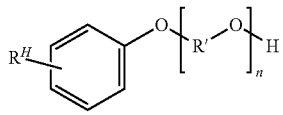

wherein $R^H$ is one or more hydrophobic, aliphatic moieties as defined above; R' is a divalent alkylene moiety of 1 to 6, preferably 1 to 4, more preferably 2 carbon atoms; and n is 2 to 100, preferably 4 to 20 on average. Example of nonionic surfactants containing the polyalkylene oxide and aromatic hydrophobic features defined above are available under trade designations including TRITON (the Dow Chemical Co.), TERGITOL (the Dow Chemical Co.), IGEPAL (Sigma-Aldrich), NONIDET (Air Products and Chemicals, Inc.), MAKON (Stepan Co.), NEUTRONYX (Stepan Co.), and the like. TRITON™ X-100 is an example of a preferred nonionic surfactant that optionally can be used in combination with one or more other surfactants.

Another useful class of nonionic surfactants includes biodegradable nonionic surfactants derived from one or more seed oils. This class has excellent wetting and detergency characteristics, as well as excellent formulation and handling properties. These surfactants feature substantially no aqueous gel ranges, rapid dissolution even in cold water, fast foam collapse rates, and compatibility with a wide range of solvents. Examples of these are commercially available under the ECOSURF trade designation from The Dow Chemical Co. and include the ECOSURF SA-4, ECOSURF SA-7, ECOSURF SA-9, and ECOSURF SA-15 surfactants singly or in combination.

Another useful class of nonionic surfactants includes one or more hydrophobic, branched, secondary alcohols that are functionalized with one or more hydrophilic alkylene oxide chains. Examples of these are commercially available from The Dow Chemical Co. under the TERGITOL and/or TMN trade designations. A specific example includes the TERGITOL™ TMN-10 surfactant.

The amount of one or more surfactants included in the corrosion inhibiting compositions can vary over a wide range. Exemplary compositions include 0.01 to 100 parts by weight of surfactant per 0.01 to 100 parts by weight of bis-imidazoline compound(s) included in the composition. In one mode of practice using 1 part by weight of surfactant per 1 part by weight of bis-imidazoline would be suitable. In another mode of practice, using 10 parts by weight of surfactant per 1 part by weight of bis-imidazoline would be suitable.

The corrosion inhibiting compositions can be used to inhibit corrosion in a wide variety of systems. For example, the compositions can be used as water treatment additives where it is desired to inhibit corrosion of a metal article that is in direct contact with water or indirect contact under conditions such that corrosion is a risk. The corrosion inhibiting compositions can be used in exemplary systems such as industrial cooling water systems, automotive cooling water systems, marine cooling water systems, gas scrubbing systems, steam generating systems, evaporation systems, water-based refrigeration systems, shipping containers, milling, boring, cutting, sawing, or machining systems, hydraulic systems, scouring systems, and the like.

Materials intended to be protected from corrosion using the corrosion inhibiting compositions can be pure metals, metal alloys, intermetallic compositions, or any other metal containing material that is at risk of corrosion. Such materials may incorporate one or a combination of metals, such as iron, copper, aluminum, zinc, nickel, tungsten, silver, chromium, lead, combinations of these, and the like. The corrosion inhibiting compositions of the present invention are particularly useful to protect ferrous metals from corrosion. Ferrous metals are any Fe(II)-containing metal, metal alloy, intermetallic composition, or any other Fe(II)-containing material (e.g., oxides, nitrides, carbides, or other compounds of Fe(II)) that might be at risk of corrosion.

The present invention will now be further described with respect to the following illustrative examples.

Example 1

Synthesis of Bis-Imidazoline

This example describes preparing the bis-imidazoline compound 18 (also referred to in these examples and the corresponding data as "LTBI") according to reaction scheme 10 shown in FIG. 1. Refined oleic acid 14 was taken in a round bottom flask and heated under agitation. Linear triethylenetetramine 12 (L-TETA, >99% purity) in the stoichiometric ratio of 1:2 moles of L-TETA to oleic acid was gradually added to the RBF at 150° C. and atmospheric pressure under agitation. The reaction mass was maintained under these conditions for up to 4 hrs. The reaction set-up was fitted with a condenser and receiver assembly to recover the water generated (~2 moles/mole of I-TETA) during the amide formation step 100 as well as the bis-imidazoline ring formation in the next step 102. To carry out step 102, the bis-amide was further heated and then maintained in the temperature range 180° C. to 220° C. under vacuum (preferably <1 mbar) and agitation for up to 5 hrs to drive the imidazoline ring formation step 102 with removal of the by-product water (~2 moles water per mole of L-TETA). The reaction completion was confirmed by the analysis of the mixture for no residual amide and complete imidazoline conversion using LCMS and NMR analysis. No catalyst or solvent was used in the reaction scheme 10.

Example 2

Synthesis of Bis-Imidazoline Salt (LTBIS)

This example describes preparing a bis-imidazoline salt (also referred to in these examples and the corresponding data as "LTBIS"). Refined oleic acid was taken in a round bottom flask and heated under agitation. Linear triethylenetetramine (L-TETA, >99% purity) in the stoichiometric ratio of 1 mole of L-TETA per 2 moles oleic acid was gradually added to the flask at 150° C. and atmospheric pressure under agitation. The reaction mass was maintained under these conditions for up to 4 hrs to form a bis-amide. The reaction set-up was fitted with a condenser and receiver assembly to recover the water generated (~2 moles/mole of L-TETA) during the bis-amide formation. To convert the bis-amide to a bis-imidazoline, the temperature of the product mixture was increased while also reducing pressure. Specifically, the bis-amide was further maintained at 220° C. under vacuum (preferably <1 mbar) and agitation for up to 5 hrs to drive the imidazoline ring formation step while removing the water by-product (~2 moles/mole of 1-TETA). The reaction completion was confirmed by the analysis (NMR, LCMS) of the mass for no residual amide and complete imidazoline conversion. No catalyst or solvent was used in the reaction scheme to form the bis-amide or the bis-imidazoline.

Next, the bis-imidazoline is quaternized with an alkylating agent. To the bis-imidazoline, dimethyl sulfate (2-4:1 moles/mole of bis-imidazoline) was gradually added under agitation and the reaction mass maintained in the range 80° C. to 130° C. for 3 hrs under reflux. The cationic surfactant (quaternized bis-imidazoline salt) was analyzed and found to have a surface tension of 30-40 mN/m and a critical micellar concentration of 2-8 ppm.

Example 3

Corrosion Inhibition Performance

Corrosion inhibition performance was evaluated in Examples 3-5 herein using a metal coupon testing protocol based on the guidelines of the ASTM G31-72 standard. Mild steel coupons fabricated as per IS 513 and sized 50 mm×25 mm×2 mm were used as test pieces for the evaluation. Dilute hydrochloric acid (15.0% w/w) was used as the test solution and was maintained at a temperature of 50° C. under agitation at a speed of 300 rpm during the test period. This represents a fairly common metal-media combination found in different industries (e.g. oil and gas industries). In the control run, the metal coupon was cleaned/dried and weighed before the trial, then immersed in the dilute acid solution under the process conditions for 6 hours, then removed from the solution, then cleaned/dried, and then weighed again. The mass loss of the coupon was used as a measure of the extent of corrosion in the test piece under the test conditions. The control run, therefore, involves an experiment for which no inhibitor or other additive is used in the corrosive media. The corrosive media without any inhibitor or other additive caused the coupon to have an average weight loss of about 12 weight percent. This level of weight loss is deemed to correspond to a corrosion inhibition efficiency of zero.

The extent of corrosion of the control sample was compared to the extent of corrosion when the bis-imidazoline of Example 1 or the bis-imidazoline salt of Example 2 (corrosion inhibitor additive was added and thoroughly mixed into the test solution at a specific dosage before introducing the metal coupon in the system). The procedure for determining the weight loss of the coupon as well as the test conditions were same as those used for the control run.

Further, using the same test procedures, the corrosion inhibition performance of the bis-imidazoline compound of Example 1 also was evaluated in the presence of additional formulation components and at more than one concentration as described in Examples 3 to 5 herein.

Further, using the same test procedures and as described in Examples 3-5 below, the corrosion inhibition performance of the bis-imidazoline compound of Example 1 and the salt of Example 2 also were compared to the corrosion protection provided by a DETA based mono-imidazoline (DI or DETA imidazoline), a linear TETA-based bis-amide (LTBA), and C-TETA-based bis-amidoimidazoline (CTBI) as well as commercial products such as Amine O (BASF) and Armohib CI-219 (AkzoNobel). CTBI is an admixture comprising bis-imidazoline, imidazoline, and amide constituents derived from a tetramine admixture containing no more than 65 weight percent of linear tetramine according to Formula II. The data described herein shows that, in the absence of surfactant, CTBI provides substantially inferior protection as compared to the enriched LTBI material (Example 1) of the present invention.

The corrosion inhibition performances of the various samples were calculated as follows:

$$\% \text{ corrosion inhibition} = \left[1 - \frac{\text{mass loss with additive}}{\text{mass loss without additive}}\right] \times 100$$

Figure 2:
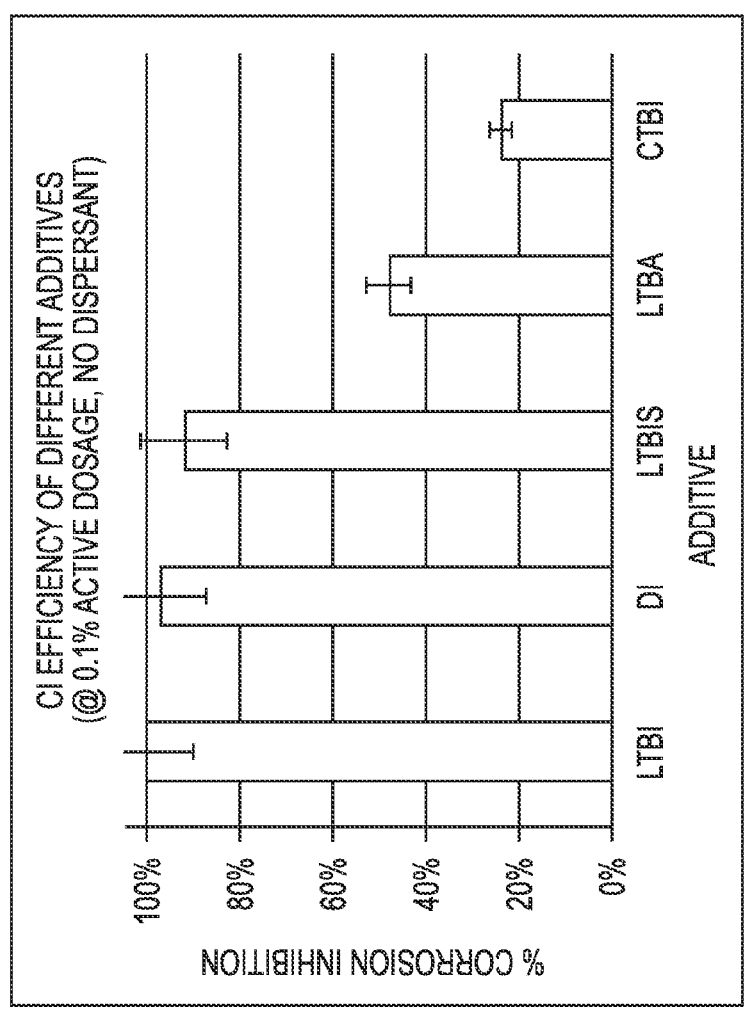
FIG. 2 shows % corrosion inhibition for samples tested at a dosage of 0.1 weight percent in acidic testing media.

FIG. 2 shows the % corrosion inhibition (% CI) of LTBI, DI, LTBIS, LTBA, and CTBI at a concentration of 0.1 weight percent in the test media without any dispersant. The results show that at such a relatively high concentration (0.1%), in absence of a dispersant, the L-TETA based bis-imidazoline of Example 1 demonstrates superior performance over all the other samples. Also, the protection provided by the LTBI (Example 1), the DI (comparison), and the LTBIS (Example 2) was dramatically better than the LTBA and CTBI comparison samples. The performance of the CTBI, which is lean in linear tetramine, is substantially inferior to the performance of the enriched LTBI.

Example 4

Figure 3:
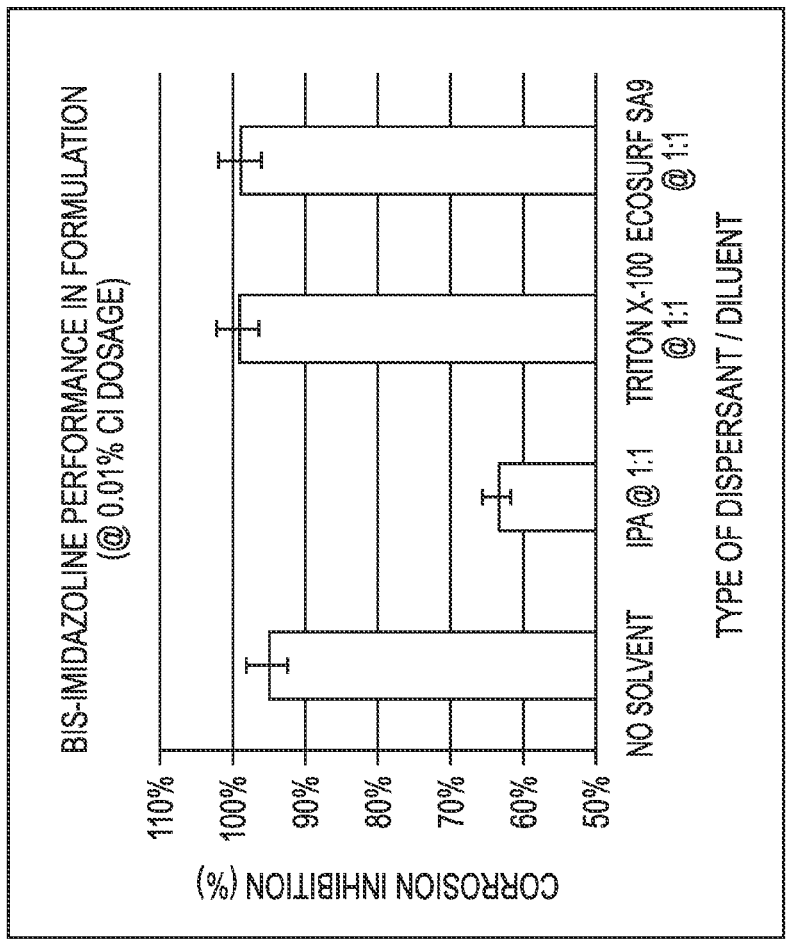
FIG. 3 shows % corrosion inhibition for samples tested at a dosage of 0.01 weight percent in acidic testing media without solvent, with solvent, with TRITON™ X-100 nonionic surfactant, and with ECOSURF™ SA-9 nonionic surfactant.

Corrosion Inhibition Performance in the Presence of Solvent and Nonionic Surfactant The test procedure of Example 3 was used to evaluate the % corrosion inhibition of the bis-imidazoline in the presence of an alcohol solvent (IPA) and two nonionic surfactants (Triton X-100 and Ecosurf SA, both available from The Dow Chemical Co.], respectively. The overall dosage of all additives used in each sample was 100 ppm. A control sample included only the bis-imidazoline as an additive at 0.01 weight percent (100 ppm) without solvent or surfactant (referred to as the "no solvent" sample) in the test media. Samples including both the bis-imidazoline and solvent or surfactant included 50 ppm of the bis-imidazoline and 50 ppm of the solvent (isopropyl alcohol, IPA) or surfactant (Triton X-100 or Ecosurf nonionic surfactant) so that the overall dosage was 100 ppm. The % corrosion inhibition of the samples is shown in FIG. 3. The data shows that using a nonionic surfactant in combination with the bis-imidazoline boosts the corrosion protection at a particular dosage of the bis-imidazoline.

Although the performance of the L-TETA based bis-imidazoline (without any diluents) reduces with concentration, in combination with a good dispersant (e.g. surfactants like Triton X-100, Ecosurf SA9, or the like), its performance is maintained even at lower active dosages. Interestingly, the dispersants/surfactants by themselves do not demonstrate any corrosion inhibition even at 0.1% dosage. This demonstrates a synergistic performance of the bis-imidazoline in combination with suitable dispersants.

Example 5

Corrosion Inhibition Performance at Reduced Dosages

The test procedure of Example 3 was used to compare the % corrosion inhibition of various corrosion inhibitors at reduced dosage in the presence of a nonionic surfactant. The bis-imidazoline of Example 1, DETA imidazoline, Amine O commercial inhibitor (BASF), and Armohib-CI-219 inhibitor (AkzoNobel) were evaluated. Each inhibitor was tested at 10 ppm in the presence of 90 ppm of the Triton X-100 nonionic surfactant. Each inhibitor also was tested at 5 ppm using 95 ppm of the Triton X-100 nonionic surfactant. Each inhibitor also was tested at 3 ppm using 97 ppm of the Triton X-100 nonionic surfactant.

Figure 4:
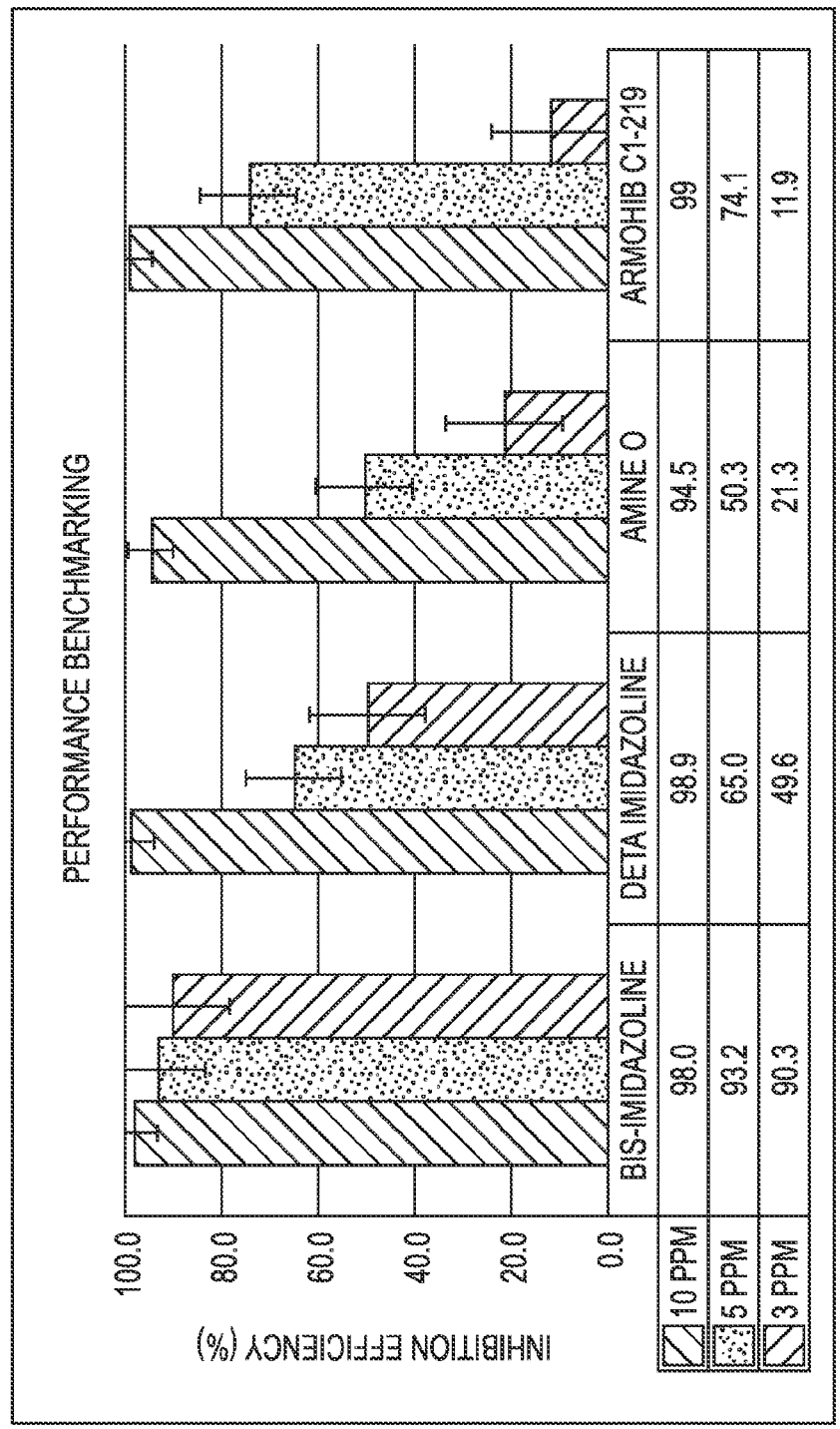
FIG. 4 shows % corrosion inhibition for samples tested in acidic testing media at 10 ppm, 5 ppm, and 3 ppm dosages in the presence of nonionic surfactant.

The performance data is shown in FIG. 4. The data shows that all of the inhibitors provided corrosion protection at the highest dosage. Even in the presence of surfactant, the corrosion protection provided by the DETA imidazoline, Amine O, and Amohib-CI-219 inhibitors and nonionic surfactant dropped considerably as the dosage of the inhibitor was reduced. The efficiency of the DETA imidazoline dropped to around 50% at 3 ppm, the Amine O efficiency dropped to around 21%, and the Amohib-CI-219 efficiency dropped to about 11%. Remarkably, however, the corrosion protection provided by the bis-imidazoline and nonionic surfactant was substantially maintained at a level of around 90% with very little drop in inhibition efficiency even when the inhibitor dosage was reduced to 3 ppm! Interestingly, nonionic surfactants by themselves generally do not demonstrate any significant corrosion inhibition even at 0.1% dosage. The data, therefore, demonstrates that the combination of a bis-imidazoline and a nonionic surfactant provides synergistic corrosion protection, particularly at lower inhibitor dosages. Whereas the natural trend is that corrosion protection drops dramatically with reduced dosage, this drop in performance is substantially avoided using principles of the present invention.

The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of inhibiting corrosion of a substrate comprising a ferrous metal, the method comprising a step of contacting the ferrous metal with composition comprising a bis-imidazoline compound and at least one nonionic surfactant, and wherein the bis-imidazoline compound has the following structure:

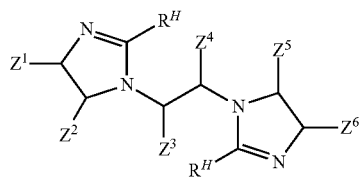

wherein:
each $Z^1$, $Z^2$, $Z^3$, $Z^4$, $Z^5$, and $Z^6$ independently is H; a hydrocarbyl of 1 to 10 carbon atoms; and/or at least first and second of the $Z^1$, $Z^2$, $Z^3$, $Z^4$, $Z^5$, and $Z^6$ moieties are linked to each other in a manner effective to form a divalent moiety that attaches to the corresponding imidazoline ring(s) at two attachment sites; and
each $R^H$ independently is a hydrophobic, aliphatic, monovalent moiety comprising 6 to 50 carbon atoms.

2. The method of claim 1, wherein the nonionic surfactant comprises (a) one or more hydrophilic polyalkylene oxide chains containing on average 2 to 100 alkylene oxide repeating units, and (b) one or more aromatic hydrophobic moieties.

3. The method of claim 1, wherein the nonionic surfactant has the structure

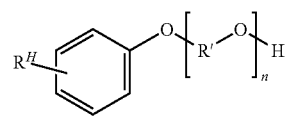

wherein $R^H$ is one or more hydrophobic, aliphatic moieties; R' is a divalent alkylene moiety of 1 to 6 carbon atoms; and n is 2 to 100 on average.

4. The method of claim 1, wherein the nonionic surfactant is derived from one or more seed oils.

5. The method of claim 1, wherein the nonionic surfactant comprises one or more hydrophobic, branched, secondary alcohols that are functionalized with one or more hydrophilic alkylene oxide chains.

6. The method of claim 1, wherein each $Z^1$, $Z^2$, $Z^3$, $Z^4$, $Z^5$, and $Z^6$ is H.

7. The method of claim 1, wherein $R^H$ is unsaturated.

8. The method of claim 1, wherein the bis-imidazoline compound has the structure

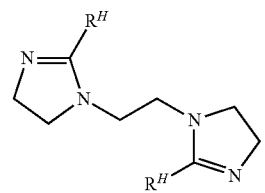

9. The method of claim 1, wherein the bis-imidazoline compound is formed from a linear tetramine that is L-TETA.

10. The method of claim 1, wherein the bis-imidazoline compound is formed from at least one linear tetramine, and at least 95 weight percent of the at least one tetramine comprises the linear tetramine.

11. The method of claim 1, wherein the composition comprises amounts of nonionic surfactant and bis-imidazoline compound of 0.01 to 100 parts by weight of nonionic surfactant per 0.01 to 100 parts by weight of bis-imidazoline compound(s).

12. The method of claim 11, wherein the composition comprises an amount of nonionic surfactant in the range of 1 to 10 parts per 1 part of bis-imidazoline compound.

13. The method of claim 1, wherein the composition comprises an amount of bis-imidazoline compound in the range of 1 ppm to 100 ppm.

14. The method of claim 1, wherein the composition comprises an amount of bis-imidazoline compound of less than 10 ppm.

15. The method of claim 1, wherein the composition comprises an amount of bis-imidazoline compound of up to 5 ppm.

16. The method of claim 1, wherein the composition comprises an amount of bis-imidazoline compound of up to 3 ppm.

17. The method of claim 1, wherein the composition comprises an amount of nonionic surfactant of up to 100 ppm.

18. The method of claim 1, wherein the composition comprises an amount of nonionic surfactant of up to 50 ppm.

* * * * *